(12) United States Patent
Verborgt et al.

(10) Patent No.: US 7,432,399 B2
(45) Date of Patent: Oct. 7, 2008

(54) DIOLS FORMED BY RING-OPENING OF EPOXIES

(75) Inventors: Jozef Verborgt, Clearwater, FL (US); Arthur Anthony Webb, Fort Washington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 355 days.

(21) Appl. No.: 10/979,843

(22) Filed: Nov. 2, 2004

(65) Prior Publication Data

US 2005/0085668 A1    Apr. 21, 2005

Related U.S. Application Data

(62) Division of application No. 10/346,061, filed on Jan. 17, 2003.

(51) Int. Cl.
| | |
|---|---|
| C07C 211/01 | (2006.01) |
| C07C 211/09 | (2006.01) |
| C07C 211/10 | (2006.01) |
| C07C 211/14 | (2006.01) |
| C07C 211/36 | (2006.01) |
| C07C 211/49 | (2006.01) |
| C07C 211/50 | (2006.01) |
| C07C 43/02 | (2006.01) |
| C07C 43/03 | (2006.01) |
| C07C 43/04 | (2006.01) |
| C07C 43/115 | (2006.01) |
| C07C 43/13 | (2006.01) |
| C07C 43/23 | (2006.01) |

(52) U.S. Cl. .............. 564/305; 564/336; 564/384; 564/388; 564/391; 564/453; 564/455; 564/461; 564/462; 564/463; 564/487; 568/583; 568/589; 568/704; 568/705

(58) Field of Classification Search ............... 564/305, 564/462, 463, 487, 336, 384, 388, 391, 453, 564/455, 461; 568/583, 589, 704, 705
See application file for complete search history.

(56) References Cited

U.S. PATENT DOCUMENTS

| | | | | | |
|---|---|---|---|---|---|
| 1,980,538 | A | * | 11/1934 | Lange | ........... 564/399 |
| 2,712,015 | A | * | 6/1955 | Bruson | ........... 544/177 |
| 3,354,209 | A | * | 11/1967 | Brack | ........... 564/443 |
| 3,367,991 | A | * | 2/1968 | Hicks | ........... 525/511 |
| 3,928,287 | A | * | 12/1975 | Jellinek et al. | ........... 528/60 |
| 4,148,772 | A | * | 4/1979 | Marchetti et al. | ........... 523/415 |
| 4,163,815 | A | * | 8/1979 | Cheung | ........... 427/385.5 |
| 4,166,132 | A | * | 8/1979 | Kraska | ........... 514/668 |
| 4,182,898 | A | * | 1/1980 | Fujiwara et al. | ........... 560/26 |
| 4,520,185 | A | | 5/1985 | Tosh | |
| 4,569,951 | A | | 2/1986 | Nelson | |
| 4,940,770 | A | * | 7/1990 | Speranza et al. | ........... 528/111 |
| 6,331,583 | B1 | * | 12/2001 | Walker | ........... 523/404 |
| 6,506,921 | B1 | * | 1/2003 | Wilkes et al. | ........... 556/413 |
| 6,723,821 | B2 | | 4/2004 | Smith | |
| 2002/0045724 | A1 | * | 4/2002 | Tsuruta et al. | ........... 528/78 |
| 2002/0086923 | A1 | * | 7/2002 | Noda et al. | ........... 524/236 |
| 2002/0091195 | A1 | * | 7/2002 | Paar et al. | ........... 525/54.11 |
| 2002/0091223 | A1 | * | 7/2002 | Walker et al. | ........... 528/87 |

FOREIGN PATENT DOCUMENTS

| | | | |
|---|---|---|---|
| DE | 442024 | * | 3/1927 |
| EP | 1277829 | * | 1/2003 |
| JP | 51-2113 | * | 1/1976 |
| JP | 53-117091 | * | 10/1978 |

OTHER PUBLICATIONS

Database Beilstein, Beilstein Inst. for Organic Chem., Frankfurt/Main, DE, XP-002282869, Registry No. 4306409, Abstr: Lovett, J. Org. Chem. v 56 No. 9, 1991.*

Database Beistein, Beilstein Inst. for Organic Chem., Frankfurt/Main, DE, XP-00228870, Registry No. 2241816, Abst: Barbelescu et al., Rev. Chim. v 22, p. 645, 1971.*

* cited by examiner

*Primary Examiner*—Rabon Sergent
(74) *Attorney, Agent, or Firm*—John J. Karasck; Joseph T. Grunkemeyer

(57) ABSTRACT

A polyol monomer comprising the formula:

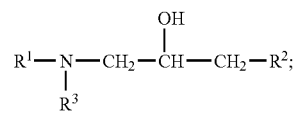

$R^1$ and $R^3$ are —H, aliphatic, aromatic, or ether; $R^2$ is aliphatic, aromatic, ester, ether, or acrylic, and $R^1$ contains a hydroxyl group, $R^3$ contains a hydroxyl group, $R^2$ contains —O—$CH_2$—CH(OH)—, or any combination thereof. The polyol monomer may be made by reacting an epoxy and an amine. Either the epoxy contains more than one epoxide groups, the amine contains a hydroxyl group, or both. A thermoset made by reacting the polyol monomer with a polyisocyanate.

7 Claims, No Drawings

DIOLS FORMED BY RING-OPENING OF EPOXIES

This nonprovisional patent application is a divisional application of U.S. patent application Ser. No. 10/346,061 filed on Jan. 17, 2003, incorporated herein by reference.

BACKGROUND OF THE INVENTION

1. Field of the Invention

The invention relates generally to the formation of diols and polyols and formation of polyurethanes therefrom.

2. Description of the Prior Art

Epoxy compounds have been reacted with amines to form thermosets. However, there have not been reports of the formation of low molecular weight products of epoxies and amines, suitable for solvent-free reaction with an isocyanate.

Polyurethanes have been made from alcohols and isocyanates. These reactions may cure quickly, even at low temperatures. The polymers are generally flexible, tough, and have good adhesion, but have inferior chemical resistance in comparison to epoxy resins. Polyurethanes can suffer from cathodic disbondment, in general due to the nature of the diols, which are susceptible to hydrolysis under alkaline conditions. Polyether diols are also used, but suffer from high water pick-up. The traditional focus for polyurethanes has been for the decorative and automotive markets.

It is known that a polymer containing multiple hydroxyl groups can be cross-linked with isocyanates. However, the starting polymer may be a solid or have a high viscosity. The polymer may need to be dissolved in a solvent in order to perform the cross-linking. The solvent must then be removed from the system, typically by evaporation.

It is also known that polymers with terminal hydroxyl groups, such as poly(ethylene glycol), may also be cross-linked with an isocyanate. These polymers may also be a solid or have a high viscosity, requiring the use of a solvent.

It is also known that a low molecular weight polyol, such as low molecular weight poly(ethylene glycol) can be cross-linked with an isocyanate. These polyols suffer from the drawback that they are not compatible or soluble in the isocyanate.

Low molecular weigh esters and acrylics have been reacted with isocyanates to form thermosets. However, these polymers suffer from hydrolysis under alkaline conditions.

There is need for a polyol monomer that is compatible with isocyanates, such it can cross-link with a polyisocyanate without the need for solvent. The desirable system would have the chemical resistance of a polyepoxide and the curing and mechanical properties of a polyurethane.

SUMMARY OF THE INVENTION

The invention comprises a polyol monomer comprising the formula:

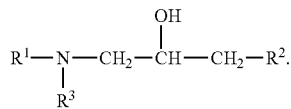

$R^2$ is selected from the group consisting of aliphatic, aromatic, ester, ether, or acrylic group; and $R^1$ and $R^3$ are independently selected from the group consisting of —H, aliphatic, aromatic, and ether. $R^1$ contains a hydroxyl group, $R^3$ contains a hydroxyl group, $R^2$ contains —O—$CH_2$—CH(OH)—, or any combination thereof.

The invention further comprises a thermoset formed by reacting a polyisocyanate with the above polyol monomer.

The invention further comprises a process of making a thermoset comprising the steps of: providing an epoxy and an amine; wherein either the epoxy contains more than one epoxide groups; the amine is selected from the group consisting of primary amines, primary amino alcohols, secondary amino alcohols, and polyamines; or both; reacting the epoxy with the amine to make a polyol monomer; and reacting the polyol monomer with a polyisocyanate.

The invention further comprises a process of making a thermoset comprising the steps of: providing the above polyol monomer and reacting the polyol monomer with a polyisocyanate.

DETAILED DESCRIPTION OF THE PREFERRED EMBODIMENTS

The polyol monomer can be made by reacting certain classes of amines with certain classes of epoxy compounds. Instead of the usual polymerization of these materials, a smaller molecule is formed. There may be no chain growth beyond a central epoxy or amine reacting in one or more epoxide ring-opening reactions. The resulting polyol monomer will have at least one secondary hydroxyl group and one or more primary and/or secondary hydroxyl groups. The monomer must have at least two hydroxyl groups in order to form a thermoset with a polyisocyanate. This may be achieved by using a primary amines, a primary amino alcohol, a secondary amino alcohol, a polyamine, or a polyepoxy. The polyol monomer may be nonsaponifiable.

In one embodiment, shown in formula (1), a secondary amino alcohol is reacted with a monoepoxy in a ring opening reaction. Throughout the specification and claims, the prefix poly-, as in polyol and polyfunctional, means two or more of the specified functional group. This results in a polyol monomer having at a secondary hydroxyl group from the reacting epoxide group and the primary or secondary hydroxyl groups from the amine. Although the alcohol group can also react with an epoxy, the amine reaction is very highly favored. An alcohol ring-opening reaction can be ignored.

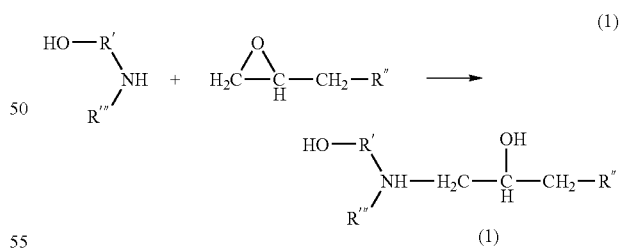

Examples of this embodiment include, but are not limited to, the products of the reaction of diethanolamine or methyl (2-hydoxypropyl)amine with butyl glycidyl ether.

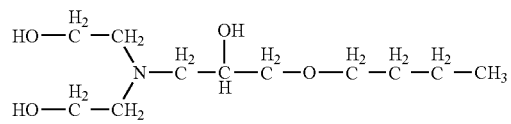

-continued

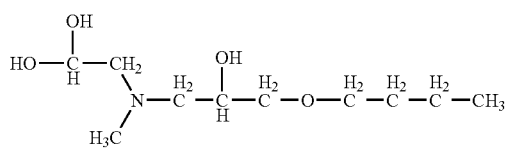

In another embodiment, shown in formula (2), a primary amino alcohol is reacted with a monoepoxy. A primary amine can react with two epoxies. This results in a polyol monomer having a secondary hydroxyl group from each epoxy and another hydroxyl group, either primary or secondary, from the alcohol. This embodiment can be varied by using less than two moles of epoxy per mole of primary amino alcohol to leave some amino hydrogens in the product.

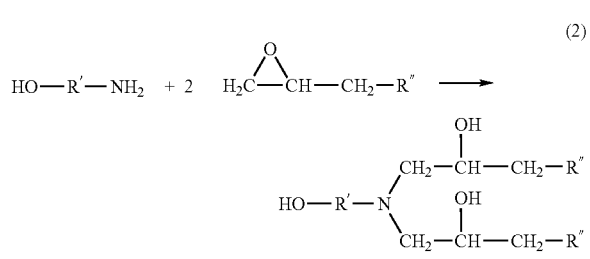

(2)

Examples of this embodiment include, but are not limited to, the product of the reaction of ethanolamine with phenyl glycidyl ether.

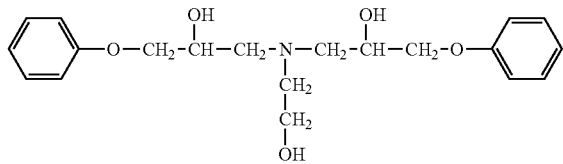

In another embodiment, a secondary amino alcohol is reacted with a polyepoxy. Sufficient amine may be used to react with all epoxies. This will also help avoid any reaction of hydroxyl groups with epoxide group. The resulting polyol monomer has at least two secondary hydroxyl groups from the polyepoxy, and primary or secondary hydroxyl groups from the amine as shown in formula (3). This embodiment can be varied by using a secondary amine instead of a secondary amino alcohol, which would result in no primary hydroxyl groups

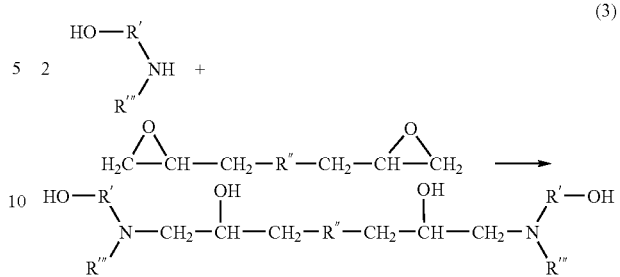

(3)

Examples of this embodiment include, but are not limited to, the product of the reaction of methylethanolamine with triglycidyl ether of glycerol.

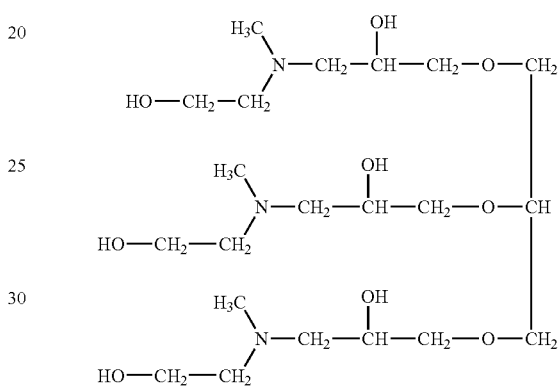

In another embodiment, a primary amine is reacted with a monoepoxy. Since a primary amine can react with two epoxies, there can be at least a 2:1 ratio of epoxy to amine. Otherwise, the product may not have two hydroxyl groups. This embodiment is shown in formula (4).

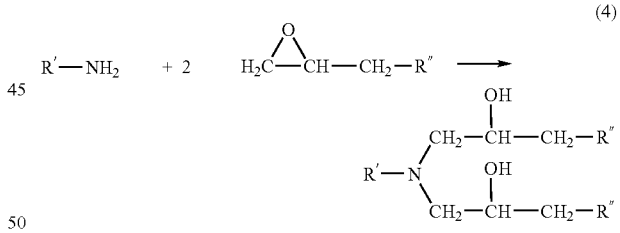

(4)

Examples of this embodiment include, but are not limited to, the product of the reaction of benzylamine with butyl glycidyl ether.

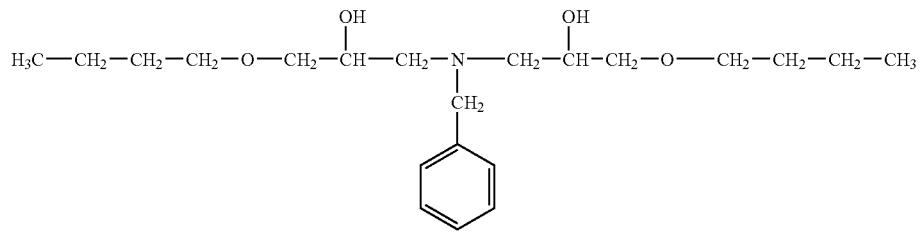

In another embodiment, a polyamine is reacted with a monoepoxy. The polyamine may include primary and/or secondary amines. This may produce only secondary amines. This embodiment is shown in formula (5). The ratio of epoxy to amine may depend on the number of available amino hydrogens. The R' and R''' groups may be aliphatic, substituted aliphatic, aromatic, substituted aromatic, and amine. The substituents may include hydroxyl groups, providing additional functionality for the subsequent reaction with a polyisocyanate. The nitrogens, R', and R''' may form a cyclic polyamine as in piperazine.

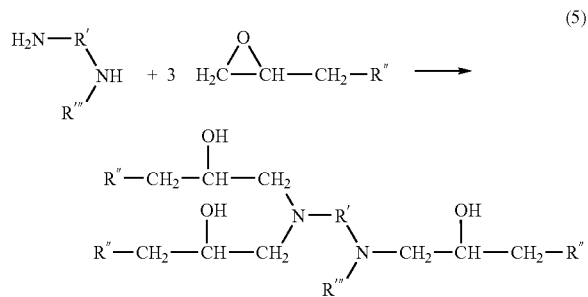

Examples of this embodiment include, but are not limited to, the product of the reaction of diethylenetriamine with butyl glycidyl ether.

contains —O—CH$_2$—CH(OH)— (formula (3)). Such an R$^2$ group contains a hydroxyl group. It may also be the case that combinations of R$^1$ and R$^3$ with R$^2$ contain hydroxyl groups (formula (3)).

The polyol monomer may have a viscosity suitable for reacting with an isocyanate under ambient conditions in the absence of a solvent. When the viscosity is too high, it may not be possible to achieve adequate mixing with the polyisocyanate to form a thermoset. It may also be possible to reduce the viscosity of the polyol monomer to a suitable viscosity by reacting it with the polyisocyanate at an elevated temperature. Suitable polyol monomers may have molecular weights in the range of about 200 to about 3000.

Reactions between a secondary amine that is not an alcohol and a monoepoxy do not ordinarily produce a polyol monomer. The result has a single secondary hydroxyl group. Such a compound can be used as an additive as described below. An exception would be a diepoxy, where one epoxide group had previously reacted with an alcohol or amine, making a monoepoxy having a hydroxyl group. Such a monoepoxy could be reacted a secondary amine to produce a polyol monomer. The product would be that of formula (3). Another exception would be a primary amine, where one amino hydrogen had previously reacted with an epoxy. The other amino hydrogen could then react with another epoxy. The product would be that of formula (2) or (4).

The R$^1$R$^3$N— group can be described as a residue of an amine, meaning that this moiety originated in an amine that reacted with an epoxy. Suitable amines include, but are not

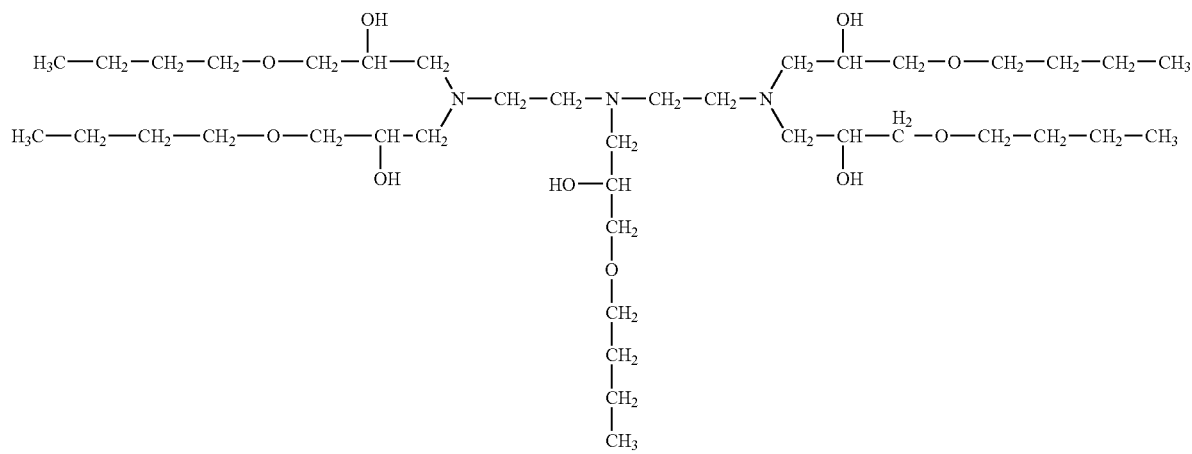

All these embodiments are encompassed by the general structure:

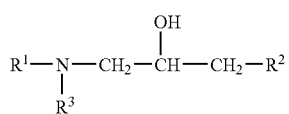

R$^1$ and R$^3$ can be —H, aliphatic, aromatic, or ether, and R$^2$ can be aliphatic, aromatic, ester, ether, or acrylic. The monomer has at least two hydroxyl groups: the one shown in the general structure, and at least one in R$^1$, R$^2$, or R$^3$. R$^1$ and/or R$^3$ contain a hydroxyl group when the amine is an amino alcohol (formulas (1), (2), and (3)), when the amine is a primary amine (formulas (2) and (4)), and when the amine is a polyamine (formula (5)). When the epoxy is a polyepoxy, R$^2$ limited to, diethanol amine, ethanolamine, butyl amine, 2-amino-methyl-1-propanol, N-methyl-(2-propanol)amine, 2-butyl-aminoethanol, N-methylethanolamine, 2-methyl isopropanol amine, 2,2-ethoxy ethanol amine, methyl ethanol amine, benzyl ethanolamine, tert-butyl amine, diethyl amine, dipropyl amine, aniline, benzylamine, 4-hydroxybenzylamine, cyclohexane diamine, ethylene diamine, diethylene triamine, isophorone diamine, N-β-hydroxyethyl ethylene diamine, m-xylylene diamine, dibutyl amine, a polyamine, a substituted polyamine, and a cyclic amine.

The R$^2$—CH$_2$—CH(OH)—CH$_2$— group can be described as a residue of an epoxy, meaning that this moiety originated in an epoxy that reacted with an alcohol. Suitable epoxies include, but are not limited to, a glycidyl ether, butyl glycidyl ether, phenyl glycidyl ether, p-tertiary butyl phenyl glycidyl ether, C$_8$-C$_{14}$ alkyl glycidyl ether, cresyl glycidyl ether, 2-ethylhexyl glycidyl ether, p-cumenol glycidyl ether, glycidyl ester of neodecanoic acid, diglycidyl ether of cyclohexane, diglycidyl ether of resorcinol, diglycidyl ether of bisphenol A, diglycidyl ether of bisphenol F, diglycidyl ether of 2-methyl resorcinol, diglycidyl ether of 1,4-butanediol, diglycidyl ether of neopentyl glycol, diglycidyl ether of 2,2-di(1,4-cyclohexyl)propane, and triglycidyl ether of glycerol.

It is to be understood that polyol monomers made from combinations of more than one amine and/or epoxies are within the scope of the claimed invention. Similarly, the inclusion of an alcohol, in the manner disclosed in the U.S. Patent application No.10/346,099, filed on Jan. 07, 2003, incorporated by reference, is also Within the scope of the claimed invention. This is also the case for thermosets made from these polyol monomers and methods of making the same.

The $R^2$ can be such that it contains no more than one —O—CH$_2$—CH(OH)— group in the same linear chain as $R^1R^3N$—. This polyol monomer would not include a polymerized epoxy. The polyol monomer may also be soluble in an isocyanate. Generally, a lower molecular weight polyol may be less compatible with isocyanates because they contain a higher percentage of polar hydroxyl groups.

The reaction of the amine and the epoxy can be performed by any means known in the art. The reaction may occur very quickly such that no catalyst or solvent is required.

The reaction may be controlled through steric hindrance by choosing the starting materials to form a secondary or tertiary structure. The molar ratio of the amine and epoxy may be chosen to result in a desired degree of reaction and quantity of hydroxyl groups. The polyol monomer may be less compatible with aliphatic isocyanates than with other isocyanates.

A thermoset can be formed by reacting the polyol monomer with a polyisocyanate according to formula (6).

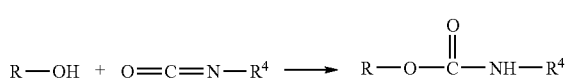

(6)

R—OH represents the polyol monomer as described above. The hydroxyl group can be from the original amine, or can be generated from the reaction of amine and epoxy. The formula shows only a single cross-link. The R group has at least one other hydroxyl group and the $R^4$ group has at least one other isocyanate group so that a thermoset is formed. An example possible structure of the thermoset is shown below.

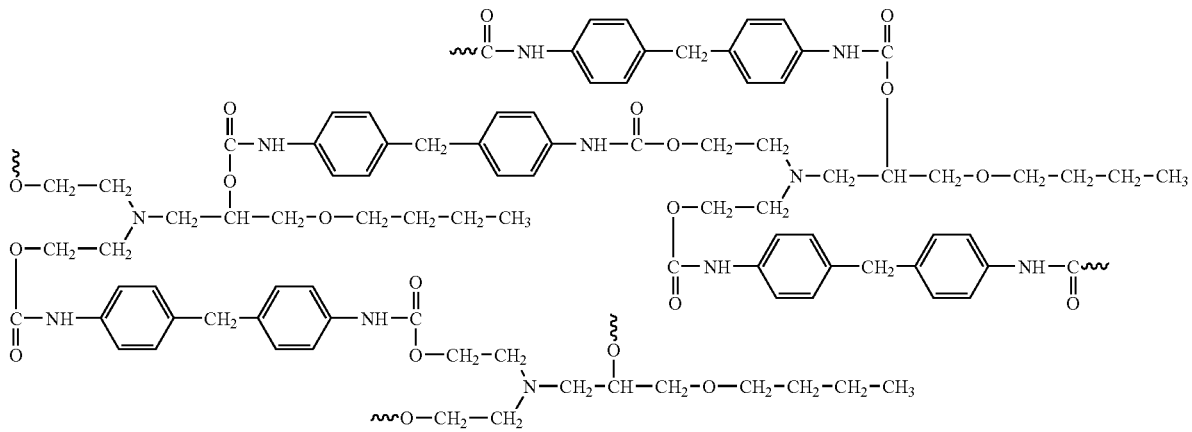

The polyol monomer was made from butyl glycidyl ether and diethanolamine. Such a polyol monomer can then be reacted with diphenylmethane diisocyanate.

When the polyol monomer is soluble in the polyisocyanate, the reaction can be solvent free. This results in no release of volatile organic compounds. The reaction can be performed by any means known in the art. The reaction can be catalyzed by any catalyst known in the art to catalyze this reaction including, but not limited to, organometallic catalysts including those based on Sn, K, Ti, and Zn and tertiary amine catalysts.

There are three commonly available types of isocyanates. Aromatics include toluene diisocyanate and diphenyl methane diisocyanate. Aliphatics include hexamethylene diisocyanate dimers and trimers, 4,4'-dicyclohexylmethane-diisocyanate, and isophorone diisocyanate. Others include tetramethylxylene diisocyanate. Other suitable polyisocyanates include, but are not limited to, hexamethylene diisocyanate, diphenylmethane diisocyanate, cycloaliphatic polyisocyanates, aliphatic polyisocyanates, an isocyanurate, biuret of toluene diisocyanate, and biuret of hexamethylene diisocyanate.

These monomeric isocyanates may have some hazards in their high reactivity and health risks. These problems may be improved by the used of polymeric isocyanates such as isocyanurate, adduct of TDI and glycerin, biuret of TDI, and biuret of HDI. As used herein, the term "polyisocyanate" includes both monomeric isocyanates and polymeric isocyanates that contain more than one isocyanate functional group. As used herein, the term "polyisocyanate " includes both monomeric isocyanates and polymeric isocyanates that contain more than one isocyanate functional group, and the mention of any polyisocyanate includes both monomeric and polymeric forms.

A variety of polyisocyanates are commercially available from Bayer including Desmodur N aliphatic isocyanates based on hexamethylene diisocyanate (N3200, N3300, and N3600), Desmodur W bis(4-isocyanatocyclohexyl) methane, and Mondur CD, MRS, and E based on diphenylmethane diisocyanate.

Generally, primary hydroxyl groups are more reactive with the polyisocyanate than secondary hydroxyl groups. The amine, epoxy, and polyisocyanate can be chosen to produce a thermoset with desired properties including degree of cross-linking, mechanical properties, adhesion, and chemical resistance.

The polyol monomer and the polyisocyanate may be mixed in a stoichiometric ratio. The polyol monomer and the polyisocyanate may be stored separately and mixed together when needed to make the thermoset. The mixture can be applied as a coating, as the mixture may have a low viscosity suitable for forming coatings. The mixture can then cure to form the thermoset. Curing times may be from a few seconds to the order of minutes and may be done at any temperatures including, but not limited to, about 10° C. or below. The reaction may proceed more favorably when there is no contamination by water. Water may cause porosity or foaming.

The polyol monomer and the polyisocyanate can be mixed together as they are sprayed onto a surface to be coated with the thermoset. This method allow for little to no reaction until the mixture has been applied to the surface. The spraying may be done with plural component spray equipment, which may include a static mixer and/or an impingement mixer.

It may be desirable to react the polyol monomer and polyisocyanate with an alcohol additive so that the viscosity of the reaction mixture is lower. The additive has a lower viscosity than that of the polyol monomer. The additive may be a monofunctional alcohol or a polyol. A monofunctional alcohol may be made by reacting a secondary amine that is not an alcohol with a monoepoxy, as shown in formula (7). The products of formulas (1) through (5) may also be used. $R^1$, $R^2$, and $R^3$ may be the same or different from those in the polyol monomer. However, using the same $R^1$, $R^2$, and $R^3$ may not have a lower viscosity than the polyol monomer.

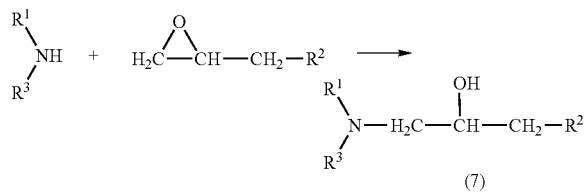

(7)

An advantage of using this monofunctional alcohol additive is that is may be chemically similar to the polyol monomer. The lower viscosity of the additive can help to reduce the viscosity of the reaction mixture, as would a solvent. However, unlike a solvent, the additive reacts with the polyol monomer and polyisocyanate and is consumed in the reaction. Since the incorporated additive is chemically similar to the polyol monomer, the properties of the thermoset are not substantially affected by the presence of the additive.

The additive may also be made by the method disclosed in the previously referenced U.S. patent application No.10/364,099. Other low molecular weight alcohols may also be used. The choice may depend on the desired amount of viscosity reduction.

The thermoset may have desirable toughness, abrasion resistance, flexibility, and adhesion strength as is generally found in polyurethanes. The thermoset may also have the chemical resistance, including hydrolytic stability and cathodic protection, of an epoxy resin. It may be resistant to caustic soda, methanol, and hydrocarbon fuel. The properties can be adjusted to form materials from tough, hard films to soft, pliable materials, fitting a wide range of applications. The properties are highly dependant on the starting materials used. The properties may be designed into the thermoset by choosing the isocyanate or combination of isocyanates, degree of polymeric isocyanate formation, and choice of polyol monomer.

The thermoset may be useful as a coating, which can be made as described above. Suitable substrates for the coating include, but are not limited to, steel, metal, and concrete. A tank lining is one application of such a coating. Such a lining may have good adhesion and chemical resistance. It may not be necessary to use a primer or topcoat.

The thermoset may also be useful as a repair compound. Higher viscosity materials than are used for coatings may be appropriate, as the compound may fill a three-dimensional void.

A composite may also be made using the thermoset by reacting the polyol monomer and the polyisocyanate in the presence of a fiber material, such as glass fibers or carbon fibers. The fibers may impart additional mechanical strength to the composite.

Having described the invention, the following examples are given to illustrate specific applications of the invention. These specific examples are not intended to limit the scope of the invention described in this application.

EXAMPLE 1

General procedure for forming the polyol monomer—Charge a 500 mL three-neck vacuum flask with the appropriate stoichiometric ratio of the epoxy and the amine. Use approximately 0.1% excess or less epoxy to assure complete reaction (i.e. consumption) of the amine. The epoxy is added in 10% portions over a period of one hour. Begin stirring the mixture with moderate heating while noting the temperature of the mixture. When the mixture turns clear, begin watching for signs of an exotherm. The mixture will initiate or display signs of an exotherm at or around 60° C. At this point the reaction vessel is placed in an ambient temperature water bath and allowed to react until the product has reached its maximum temperature. In general the mixture will peak at 120° C. but can be higher if not placed into water bath at or around 60° C. An excessive exotherm greater than 150-160° C. should be avoided as it can result in etherification of secondary alcohols. Following the exotherm, the reaction product is then gently heated to 120° C. over a period of about one hour. The reaction product is vacuum distilled to remove all unreacted materials, water, and volatiles beginning at 120° C. and allowed to cool to approximately 90° C. Vacuum distillation continues until no further violent boiling is observed. This signifies that all moisture and unreacted glycidyl ether has been removed. Usually no more than one to three percent of volatiles are removed this way. The resulting product is cooled and placed in a suitable storage container for future use.

EXAMPLE 2

Reaction of monoepoxies with primary amines—In these reactions, two moles of a monoepoxy are reacted with one mole of a primary amine according to the procedure of Example 1. This molar ratio is used regardless of whether the amine is an amino alcohol. Combinations that were reacted included butyl glycidyl ether with benzyl amine, o-toluenyl glycidyl ether with butyl amine, phenyl glycidyl ether with ethanolamine, and butyl glycidyl ether with p-hydroxybenzylamine.

EXAMPLE 3

Reaction of monoepoxies with secondary amino alcohols—In these reactions, two moles of a monoepoxy are reacted with one mole of a secondary amino alcohol according to the procedure of Example 1. Combinations that were reacted included butyl glycidyl ether with diethanolamine and p-cumenol glycidyl ether with methylethanolamine.

EXAMPLE 4

Reaction of polyepoxies with secondary amino alcohols—In these reactions, one mole of a polyepoxy is reacted with two or more moles of a secondary amino alcohol according to the procedure of Example 1. One mole of secondary amino alcohol is used for each epoxide group in the polyepoxy. Combinations that were reacted included 1 mole diglycidyl ether of bisphenol F with 2 mole diethanolamine and 1 mole triglycidyl ether of glycerin with 3 mole methylethanolamine.

EXAMPLE 5

Reaction of monoepoxies with polyamines—In these reactions, one mole of a polyamine is reacted with two or more moles of a monoepoxy according to the procedure of Example 1. Up to one more of monoepoxy is used for each amino hydrogen in the polyamine. Combinations that were reacted included 5 moles butyl glycidyl ether with 1 mole diethylene triamine.

EXAMPLE 6

Reaction of monoepoxies with secondary amines to form an alcohol additive—In these reactions, one mole of a monoepoxy is reacted with one mole of a secondary amine according to the procedure of Example 1. This formed alcohol additives containing a single hydroxyl group. Combinations that were reacted included butyl glycidyl ether with dibutyl amine and phenyl glycidyl ether with dipropyl amine.

EXAMPLE 7

General procedure for forming the thermosets—The thermoset was made by mixing together a polyol monomer and a polyisocyanate. The mixture solidified without the use of a catalyst or heating. The thermoset was formed as a shaped article, such as a disk.

EXAMPLE 8

Formation of thermosets from ethanolamine—Polyol monomers made from the reaction of ethanolamine and a variety of monoepoxies including butyl glycidyl ether and phenyl glycidyl ether were reacted with a variety of polyisocyanates including triisocyanurates, hexamethylene diisocyanates, diphenylmethylene diisocyanates, and bis(4-isocyanatocyclohexyl) methane. All formed tough thermosets.

EXAMPLE 9

Formation of thermosets from diethanolamine—Polyol monomers made from the reaction of diethanolamine and a variety of monoepoxies including butyl glycidyl ether and phenyl glycidyl ether were reacted with a variety of polyisocyanates including triisocyanurates, hexamethylene diisocyanates, diphenylmethylene diisocyanates, and bis(4-isocyanatocyclohexyl) methane. All formed tough thermosets. The same was done with bifunctional epoxies.

EXAMPLE 10

Formation of thermosets from methylethanolamine—Polyol monomers made from the reaction of methylethanolamine and a variety of monoepoxies including butyl glycidyl ether and phenyl glycidyl ether were reacted with a variety of polyisocyanates including triisocyanurates, hexamethylene diisocyanates, diphenylmethylene diisocyanates, and bis(4-isocyanatocyclohexyl) methane. All formed tough thermosets. The same was done with bifunctional epoxies.

EXAMPLE 11

Formation of thermosets from polyamines—Polyol monomers made from the reaction of butyl glycidyl ether with polyamines including diethylene triamine, ethylene diamine, 1,2-cyclohexane diamine, xylylene diamine, isophorone diamine, and N-β-hydroxyethyl ethylene diamine were reacted with a variety of polyisocyanates including triisocyanurates, hexamethylene diisocyanates, diphenylmethylene diisocyanates, and bis(4-isocyanatocyclohexyl) methane. All formed tough thermosets.

Obviously, many modifications and variations of the present invention are possible in light of the above teachings. It is therefore to be understood that, within the scope of the appended claims, the invention may be practiced otherwise than as specifically described.

We claim:

1. A polyol monomer comprising the formula:

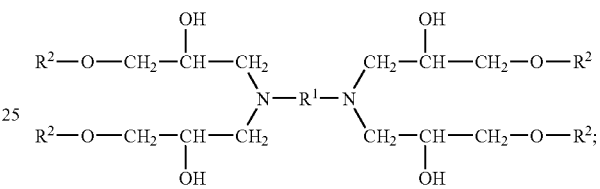

wherein $R^1$ is a divalent radical selected from the group consisting of aliphatic, aromatic, and ether-containing group;

wherein $R^2$ is free —O—$CH_2$—CH(OH)— groups;

wherein $R^2$—O—$CH_2$—CH(OH)—$CH_2$— is a residue of an epoxy selected from the group consisting of butyl glycidyl ether, phenyl glycidyl ether, p-tertiary butyl phenyl glycidyl ether, $C_8$-$C_{14}$ alkyl glycidyl ether, cresyl glycidyl ether, 2-ethylhexyl glycidyl ether, and p-cumenol glycidyl ether; and wherein the polyol monomer is free of epoxy groups and amino hydrogens.

2. The polyol monomer of claim 1, wherein the polyol monomer is soluble in an isocyanate.

3. The polyol monomer of claim 1, wherein the polyol monomer has a viscosity suitable for reacting with an isocyanate under ambient conditions in the absence of a solvent.

4. The polyol monomer of claim 1, wherein the polyol monomer has a molecular weight no more than about 3000.

5. The polyol monomer of claim 1, wherein the polyol monomer has a molecular weight no less than about 200.

6. The polyol monomer of claim 1, wherein N—$R^1$—N is a residue of a diamine selected from the group consisting of cyclohexane diamine, ethylene diamine, isophorone diamine, N-β-hydroxyethyl ethylene diamine, and m-xylylene diamine.

7. The polyol monomer of claim 1, wherein the polyol monomer is

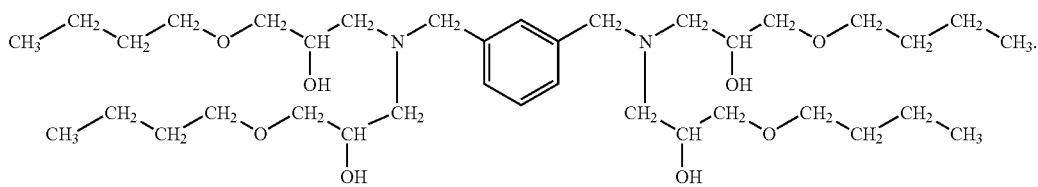

* * * * *